United States Patent [19]

Akasaki et al.

[11] Patent Number: 5,008,431
[45] Date of Patent: Apr. 16, 1991

[54] BENZOPHENONE DERIVATIVE

[75] Inventors: Yutaka Akasaki; Katsumi Nukada; Katsuhiro Sato, all of Kanagawa, Japan

[73] Assignee: Fuji Xerox Co., Ltd., Tokyo, Japan

[21] Appl. No.: 436,620

[22] Filed: Nov. 15, 1989

[30] Foreign Application Priority Data

Nov. 16, 1988 [JP] Japan ................ 63-287617

[51] Int. Cl.$^5$ .......................... C07C 255/01
[52] U.S. Cl. ....................... 558/402; 558/374
[58] Field of Search ................ 558/374, 402

[56] References Cited

U.S. PATENT DOCUMENTS 4,833,263 5/1989 Akasaki et al. ............. 558/374

FOREIGN PATENT DOCUMENTS 0912019 10/1972 Canada .................. 558/374
48-9988 3/1973 Japan ................... 558/405
54-30834 3/1979 Japan ................... 558/405

Primary Examiner—Robert W. Ramsuer
Assistant Examiner—J. Richter
Attorney, Agent, or Firm—Finnegan, Henderson, Farabow, Garrett and Dunner

[57] ABSTRACT

Benzophenone derivatives which are useful in electrophotographic light-sensitive material represented by formula (I):

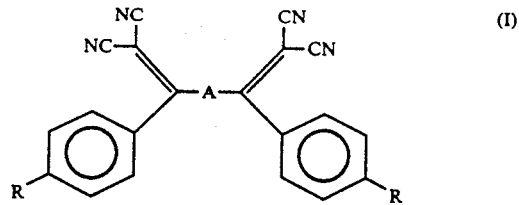

wherein A represents the structural formula (a), (b) or (c):

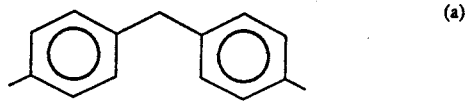

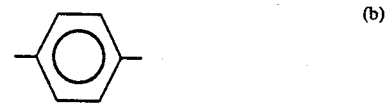

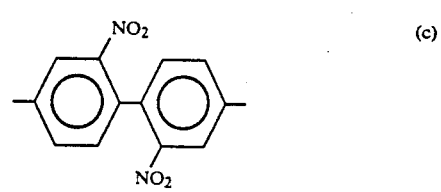

and R represents an alkyl group having 1 to 8 carbon atoms or a nitro group, and a process for preparation thereof. These benzophenone derivatives can be synthesized by reacting compounds represented by formula (II):

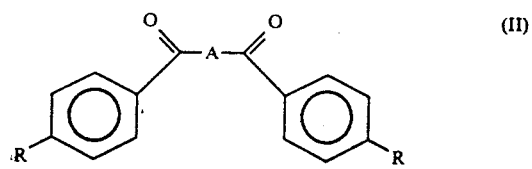

wherein A and R are the same as defined above, with malonitrile.

2 Claims, No Drawings

BENZOPHENONE DERIVATIVE

FIELD OF THE INVENTION

The present invention relates to novel benzophenone derivatives which are useful in electrophotographic light-sensitive material, and a process for the preparation thereof.

BACKGROUND OF THE INVENTION

Electrophotographic photoreceptors using an organic photoconductive substance have been extensively studied because of advantages such as no pollution, high productivity and low production cost. An electrophotographic photoreceptor containing a diphenyldicyanoethylene derivative as a sensitizer in a light-sensitive layer thereof is known as described in, for example, JP-A-54-30834 (the term "JP-A" as used herein means an "unexamined published Japanese patent application").

An organic photoconductive substance which generates an electric charge upon absorption of visible light is poor in electric charge-retaining force. Conversely, an organic photoconductive substance which is good in electric charge-retaining force and excellent in film-forming properties generally does not exhibit any substantial photoconductivity upon application of visible light. In order to overcome the above problem, a laminate type light-sensitive layer has been designed, i.e., a layer structure that is functionally separated into an electric charge-generating agent which generates an electric charge upon absorption of visible light and an electric charge-transporting agent which transports an electric charge. A number of electric charge-generating agents and electric charge-transporting agents have been proposed. Known positive hole-transporting agents include amine compounds, hydrazone compounds, pyrazoline compounds, oxazole compounds, oxadiazole compounds, stilbene compounds, carbazole compounds and the like, and known electron-transporting agents include 2,4,7-trinitrofluorenone and the like. In addition, boron-containing compounds are described, for example, as a photoconductive substance in JP-B-48-9988 (the term "JP-B" as used herein means an "examined Japanese patent publication"), and as a fluorescent agent in Canadian Patent No. 912,019.

A sensitizer, which is sufficient for use with an electrophotographic photoreceptor of a single layer structure using an organic photoconductive substance has not been known in the art. A positive charging type material is desirable for use in a function separation type electrophotographic photoreceptor of the laminate structure for preventing generation of ozone in corotron and for controlling charging of a toner in development. In the case of the positive charging type material, when the electric charge-transporting agent is positive hole-transporting, it is necessary for the electric charge-generating layer to be provided as an upper layer. The electric charge-generating layer is usually made thin in view of its function and fails to sufficiently satisfy mechanical characteristics as a photoreceptor. Moreover, some modifications should be made to a copying machine, to use it in a negative charging system. Thus a positive charging type photoreceptor having a relatively thick electric charge-transporting layer as an upper layer is desired, and in this case, it is necessary to use an electron-transporting electric charge-transporting agent in the electric charge-transporting layer. However, of electron-transporting electric charge-transporting agents conventionally proposed, no sufficiently satisfactory substance has been known.

SUMMARY OF THE INVENTION

An object of the present invention is to provide an organic photoconductive substance which is useful as an electric charge-transporting agent in a positively charging laminate type electrophotographic photoreceptor.

It has now been found that benzophenone derivatives represented by the general formula (I) as shown below are excellent as electric charge-transporting agents.

The present invention relates to a compound represented by formula (I):

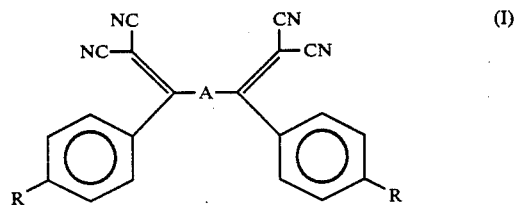

wherein A represents the structural formula (a), (b) or (c) shown below,

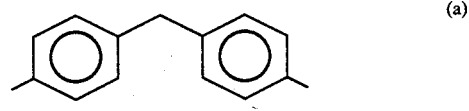

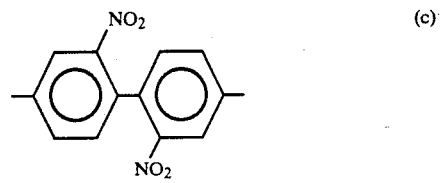

and R represents an alkyl group having 1 to 8 carbon atoms or a nitro group.

The present invention further relates to a process for preparing a compound represented by formula (I) which comprises reacting a compound represented by formula (II):

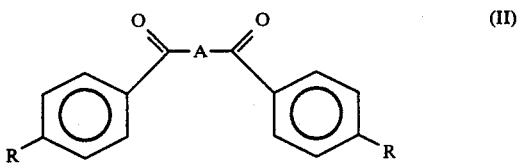

wherein A and R are the same as defined above, with malonitrile.

DETAILED DESCRIPTION OF THE INVENTION

The compounds of the present invention are represented by the following formula (I):

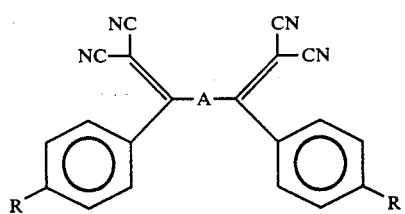 (I)

wherein A represents the structural formula (a), (b) or (c) shown below:

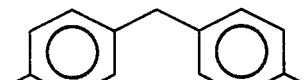 (a)

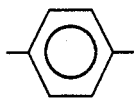 (b)

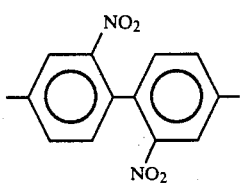 (c)

and R represents an alkyl group having 1 to 8, preferably 1 to 4 carbon atoms, or a nitro group.

Examples of the compounds represented by formula (I) in the present invention are shown below.

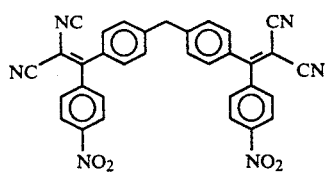 (1)

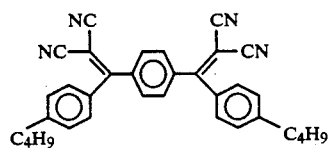 (2)

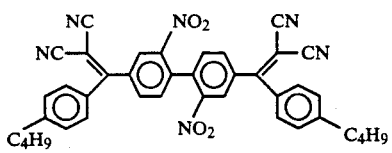 (3)

The compounds represented by formula (I) of the present invention can be prepared, as illustrated by the reaction scheme shown below, by heating under reflux compounds represented by the following formula (II) with malonitrile in a solvent, e.g., pyridine:

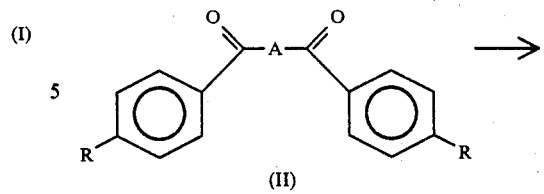 (II)

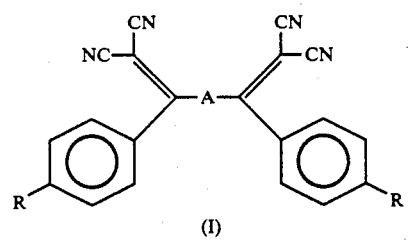 (I)

wherein A and R are the same as defined above.

The compounds represented by formula (I) of the present invention exhibit excellent electron transporting properties and when used as a sensitizer or electric charge-transporting agent for an electrophotographic photoreceptor, provide a positive charging electrophotographic photoreceptor exhibiting excellent electrophotographic characteristics.

The benzophenone derivatives represented by formula (I) of the present invention exhibit electron transporting properties superior to those of 2,4,7-trinitrofluorenone conventionally known to be relatively good, and thus are useful as sensitizers or electric charge-transporting agents for a positive charging type electrophotographic photoreceptor. For example, if after providing an electric charge-generating layer on an electrically conductive support, an electric charge-transporting layer is formed by coating the above benzophenone derivative with a film-forming resin, there is obtained a positive charging type electrophotographic photoreceptor having excellent electrophotographic characteristics.

The present invention is described in greater detail with reference to the following examples.

EXAMPLE 1

10.0 g (21.4 mmol) of a compound represented by the structural formula:

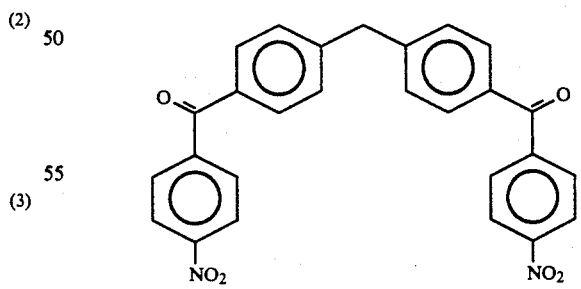

as obtained by condensing p-nitrobenzoyl chloride and diphenyl-methane, 5.7 g (85.8 mmol) of malonitrile and 80 ml of pyridine were placed in a 100-milliliter three-necked flask and refluxed in a stream of nitrogen for 3 hours, and then the pyridine was distilled away under reduced pressure. The residue was dissolved in methylene chloride, washed with diluted hydrochloric acid and then with water, dried over $Na_2SO_4$, and purified with a silica gel short column (eluted with methylene chloride). After distillation of the solvent, the residue was recrystallized from ethyl acetate to obtain 5.3 g of Illustrative Compound (1) as light orange needle-like crystals (yield 44.1%). Melting Point: 226° to 228° C.

| Elemental Analysis: | | | |
|---|---|---|---|
| | C | H | N |
| Calculated | 70.46 | 3.22 | 14.94 |
| Found | 70.71 | 3.02 | 14.84 |

Mass Spectral Analysis: M+562.
UV Absorption Spectrum: $\lambda_{max}$: 282 nm, 355 nm (in $CH_2Cl_2$).
Infrared Absorption Spectrum: 2224 cm$^{-1}$ (KBr).

EXAMPLE 2

In the same manner as in Example 1 except that 10 g (25.1 mmol) of a compound represented by the following structural formula:

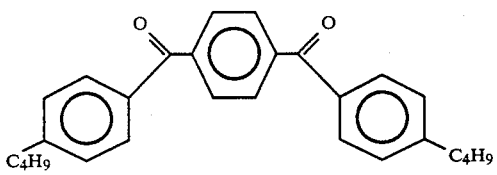

as obtained by condensing terephthaloyl chloride and n-butyl-benzene was used and the amounts of malonitrile and pyridine were 6.63 g (100 mmol) and 80 ml, respectively, 8.27 g of Illustrative Compound (2) was obtained as light yellow plate-like crystals (yield 66.6%). Melting Point: 201° to 202.5° C.

| Elemental Analysis: | | | |
|---|---|---|---|
| | C | H | N |
| Calculated | 82.56 | 6.11 | 11.33 |
| Found | 82.75 | 5.95 | 11.30 |

Mass Spectral Analysis: M+494
UV Absorption Spectrum: $\lambda_{max}$: 315 nm, 337 nm (in $CH_2Cl_2$)
Infrared Absorption Spectrum: 2224 cm$^{-1}$ (KBr)

EXAMPLE 3

15 g (26.6 mmol) of a compound represented by the structural formula:

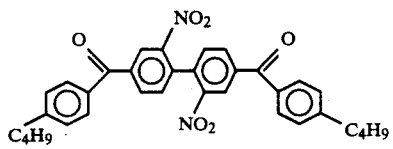

as obtained by condensing 2,2'-dinitrobiphenyl-4,4'-carboxylic acid chloride and n-butylbenzene, 7 g (106.4 mmol) of malonitrile and 80 ml of pyridine were treated in the same manner as in Example 1 to obtain 12.12 g of Illustrative Compound (3) as a light yellow powder (yield 69%). Melting Point: 231° to 232° C.

| Elemental Analysis: | | | |
|---|---|---|---|
| | C | H | N |
| Calculated | 72.71 | 4.88 | 12.71 |
| Found | 72.82 | 4.72 | 12.55 |

Mass Spectral Analysis: M+660
UV Absorption Spectrum: $\lambda_{max}$: 294 nm, 338 nm (in $CH_2Cl_2$)
Infrared Absorption Spectrum: 2224 cm$^{-1}$ (KBr)

APPLICATION EXAMPLE 1

An electric charge-generating layer (2.5 μm) comprising trigonal selenium/polyvinyl carbazole (trigonal selenium 7% by volume) was provided on an electrically conductive substance, and on the electric charge-generating layer, a solution of 0.5 g of Illustrative Compound (1) and 0.75 g of bisphenol A polycarbonate (Makrolon 5705 made by U.S. Bayer Co., Ltd.) dissolved in 7 g of methylene chloride was coated in a 5 mil of gap at the time of wetting and dried at 80° C. for 1 hour to produce an electrophotographic photoreceptor. This electrophotographic photoreceptor was charged at +800 V and −800 V by the use of an electrostatic copying paper tester (SP428 produced by Kawaguchi Denki Seisakusho Co., Ltd.) and exposed to 5 lux white light to measure sensitivity (dV/dt). The results were as follows:

| | | |
|---|---|---|
| Charged potential | +800 V | −800 V |
| Initial sensitivity (V/sec) | 534 | — |

APPLICATION EXAMPLES 2 AND 3

In the same manner as in Application Example 1 except that Illustrative Compounds (2) and (3) were used in place of Illustrative Compound (1), respectively, electrophotographic photoreceptors were produced and measured for sensitivity. The results are shown in Table 1.

COMPARATIVE EXAMPLE

In the same manner as in Application Example 1 except that 2,4,7-trinitrofluorenone (TNF) was used in place of Illustrative Compound (1), an electrophotographic photoreceptor was produced and measured for sensitivity. The results are shown in Table 1.

Table 1

TABLE 1

| | Initial Sensitivity | |
|---|---|---|
| | +800 V | −800 V |
| Application Example 2 | 85 | — |
| Application Example 3 | 175 | — |
| Comparative Example | 66 | — |

While the invention has been described in detail and with reference to specific examples thereof, it will be apparent to one skilled in the art that various changes and modifications can be made therein without departing from the spirit and scope thereof.

What is claimed is:

1. A benzophenone derivative represented by formula (I):

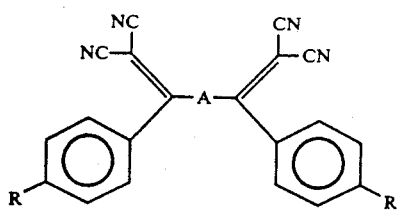
(I)
wherein A represents one of the following structural formulas (a), (b) or (c),
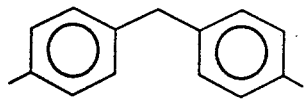
(a)
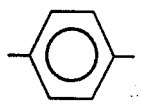
(b)
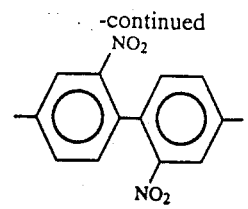
(c)
and R represents an alkyl group having 1 to 8 carbon atoms or a nitro group.
2. The benzophenone derivative according to claim 1, wherein said derivative is selected from the group consisting of
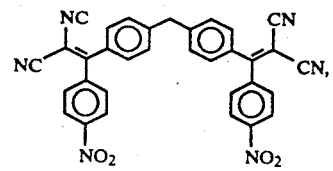
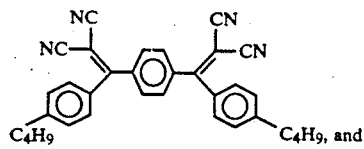
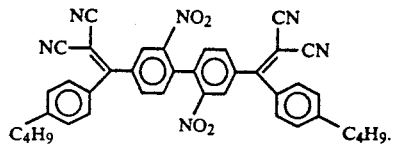
* * * * *